United States Patent [19]

Ritter et al.

[11] Patent Number: 4,933,486

[45] Date of Patent: Jun. 12, 1990

[54] PROCESS FOR THE PREPARATION OF 4-HALO-3-OXO-2-ALKOXYAMINOBUTYRIC ESTERS

[75] Inventors: Eberhard Ritter, Mörfelden-Walldorf; Claus-Peter Krieg, Frankfurt am Main; Detlev Keil, Hofheim am Taunus, all of Fed. Rep. of Germany

[73] Assignee: Hoechst Aktiengesellschaft, Frankfurt am Main, Fed. Rep. of Germany

[21] Appl. No.: 327,262

[22] Filed: Mar. 22, 1989

[30] Foreign Application Priority Data

Mar. 24, 1988 [DE] Fed. Rep. of Germany ....... 3809845

[51] Int. Cl.$^5$ .............................................. C07C 131/00
[52] U.S. Cl. .................................................... 560/168
[58] Field of Search ......................................... 560/168

[56] References Cited

U.S. PATENT DOCUMENTS 4,205,180  5/1980  Ochiai ................................ 560/168
4,480,120  10/1984  Jewel ................................. 560/168
4,845,257  7/1989  Naito ................................. 560/168

Primary Examiner—Michael L. Shippen
Attorney, Agent, or Firm—Finnegan, Henderson, Farabow, Garrett and Dunner

[57] ABSTRACT

A process for the preparation of 4-halo-3-oxo-2-alkoxyiminobutyric esters.

A process for the preparation of 4-halo-3-oxo-2-alkoxyiminobutyric esters by solvent-free halogenation of the liquid substrate of a 3-oxo-2-alkoxyiminobutyric ester with elemental halogen.

4 Claims, No Drawings

PROCESS FOR THE PREPARATION OF 4-HALO-3-OXO-2-ALKOXYAMINOBUTYRIC ESTERS

DESCRIPTION

A process for the preparation of 4-halo-3-oxo-2-alkoxyiminobutyric esters.

4-Halo-3-oxo-2-alkoxyiminobutyric esters of the general formula

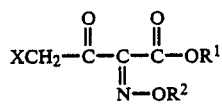

in which $R^1$ and $R^2$ represent alkyl, preferably $C_1$–$C_4$-alkyl, in particular $R^1$ represents ethyl and $R^2$ represents methyl, and X denotes halogen, preferably chlorine or bromine, are intermediates for the preparation of side-chain acids which represent an important building block in the synthesis of cephalosporin antibiotics. They are usually subjected to a Hantzsch cyclization with thiourea. Then, after hydrolysis of the ester, the acid is reacted with 7-aminocephalosporanic acid or one of its derivatives to give the amide having antibiotic activity.

One possible way of synthesizing these precursors is the methylation of 4-halo-3-oxo-2-hydroxyiminobutyric esters with diazomethane or dialkyl sulfates (German Offenlegungsschriften Nos. 2,702,501, 2,737,504 and 2,806,226 and German Patent No. 2,713,272). This reaction route suffers from the difficulty of obtaining the precursor.

Thus the halogenation of 3-oxo-2-methoxyiminobutyric esters has become widely used, for which various processes are known. All the known conversions carry out the reaction—irrespective of the halogenating agent—in an inert solvent. Those proposed include acetone, diethyl ether, formic acid, glacial acetic acid, dimethylformamide and tetrahydrofuran (EP Nos. 0,007,633, 0,049,539 and 0,191,507). Methylene chloride has become the most widely used.

The halogenating agents which have been employed are the halogens themselves, sulfuryl halide, N-halosuccinimide and pyridinium perhalides (EP No. 0,007,633). Of the halogenating agents mentioned, those which have been widely used are, in particular, sulfuryl chloride for the synthesis of the chloro compound (X=chlorine) and elemental bromine for the preparation of the analogous bromo compound. Bromination in methylene chloride takes, as a rule, one hour at room temperature, whereas chlorination with sulfuryl chloride in the same solvent requires 4 to 10 hours at 35° to 42° C. (EP Nos. 007,633, 0,059,539, 0,191,507, JA No. 56/100,772, U.S. Pat No. 4,480,120) and thus takes place considerably more slowly. Hence bromination in methylene chloride has been the more interesting procedure in practice.

With the increase in sensitivity to environmental protection and to protection of personnel from contact with chemicals injurious to health, the emission of solvent vapors in the standard process has proved to be a problem. If it were furthermore possible to make the rate of chlorination similar to that of the bromination it would be possible to replace the bromine, which is classified as highly toxic.

Hence the object was to find an alternative to methylene chloride to avoid the need to employ this critical solvent in future. However, it appeared in principle necessary to employ a solvent in order to ensure that the reaction takes place in a controlled and selective manner. At the same time, the intention was that the new process would provide the opportunity to replace bromination by chlorination, with comparable yields and in comparable times.

Initially, the suitability of other solvents acceptable in terms of occupation hygiene was examined. When this did not lead to the desired success, it was established, surprisingly, that the halogenation can be carried out with good yields even without employing a solvent.

Thus the process according to the invention comprises exposing the liquid substrate of a 3-oxo-2-alkoxyiminobutyric ester of the general formula I

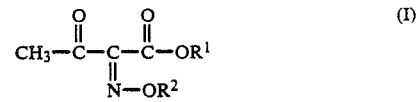

in which $R^1$ and $R^2$ represent $C_1$–$C_4$-alkyl, to the action of elemental halogen directly, without using a solvent, and thus obtaining a 4-halo-3-oxo-2-alkoxyiminobutyric ester of the general formula II .

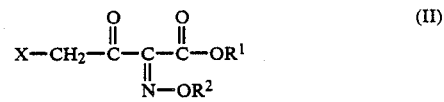

in which $R^1$ and $R^2$ have the previous meaning, and X represents halogen.

In view of the known greater importance of the syn compounds in the case of cephalosporin antibiotics, also preferred according to the invention are compounds in which the $R^2O$ group is in the syn position.

Meanings for $R^1$ and $R^2$ which may be mentioned are methyl, ethyl, n-propyl, isopropyl, n-butyl, sec.-butyl or tert.-butyl. However, compounds of the general formulae I and II in which $R^1$ represents ethyl and $R^2$ represents methyl are preferred.

Suitable and preferred for X are chlorine, bromine and iodine, especially chlorine and bromine.

The esters of the general formula I can be prepared by the process of German Offenlegungsschrift No. 2,702,501.

The process according to the invention has proved particularly suitable for the industrial bromination of 3-oxo-2-alkoxyiminobutyric esters. The experimental details had to be modified somewhat for the chlorination, but this was not, contrary to expectation, at the cost of losses of selectivity.

The process according to the invention can be carried out in the following manner, for example. The starting material in the form of an ester of the general formula I of technical grade or purified by distillation is introduced into a jacketed stirred vessel which is composed of acid-resistant material and is equipped with an internal thermometer. A pressure vessel is advantageously used for the chlorination.

For the bromination, about 0.5 to 0.8, preferably 0.6, mol of bromine is required for one mol of starting compound. At about 15°–40° C., preferably at 20° C., about 5–15%, preferably 10%, of the required amount of bromine is added, with or without, preferably without, stirring. The start of the reaction is evident from decoloration of the reaction solution and an increase in temperature, for example of 6°–10° C. The mixture is then cooled to about 10°–25° C., preferably to 15° C., and the remainder of the bromine is added, while stirring, at a rate such that the internal temperature remains constant. The progress of the reaction is observed by HPLC, and the reaction is stopped when formation of the dibrominated product starts. The hydrogen bromide which has formed is driven out with nitrogen for about 30 minutes. In practice, it is possible to employ the product without further purification, which would be possible by distillation for example, in the next reaction stage.

For the chlorination, the reaction vessel should additionally be equipped with a gas-introduction tube. In equipment for larger batches, the orifices for the gas to pass through should be chosen such that, to obtain small bubbles, gas velocities passing through of about 5–50 m/s, advantageously 10–50 m/s, preferably 20–30 m/s, are reached at a flow of chlorine which still permits the heat of reaction which is evolved to be dissipated. A suitable additional safety device is a differential pressure gage, which is coupled to a fast-acting valve, between the chlorine reservoir and the reaction vessel.

The starting material is heated to about 30°–40° C., and then the introduction of chlorine is started. After about 5–15%, advantageously 10%, of the total amount of chlorine has been added the reaction starts, which is evident from the rise in temperature. If this does not occur, the introduction is stopped and then about 0.1–2%, advantageously 0.1–1%, preferably 0.1%, of concentrated sulfuric acid or another anhydrous acid (gaseous hydrogen chloride, or acetic acid or the like) is added as catalyst to the starting material.

After the reaction has started, the introduction of chlorine is continued at about 30°–70° C., preferably 40°–50° C., especially 50° C. A total of about 1–1.4 mol, advantageously 1.2 mol, of chlorine per mol of organic substrate is introduced at such a rate that the internal temperature can be maintained.

In order to force complete conversion of chlorine in every case, the introduction can be carried out in such a way that chlorine is passed in until the differential pressure gage responds, and then the gaseous hydrogen chloride which has been produced as second reaction product is discharged into a scrubber operated with, for example, 16% strength sodium hydroxide solution. Where appropriate, these steps should be repeated until all the chlorine has been introduced. However, it is advantageous to allow the HCl gas to flow out continuously under a pressure of about 1–6 bar, advantageously 2–6 bar, preferably 3 bar, in the vessel. It is also possible to achieve conversions of chlorine exceeding 99.5% in this way.

The chlorinated product can be employed without further purification in the next stage of the synthesis.

Use of the invention results in an improved synthesis of an important building block for highly active cephalosporin antibiotics. Since a solvent is no longer required, the space-time yield is considerably increased. Problems no longer occur with solvent vapors difficult to remove from the exhaust air. Since after the halogenation method has been changed, from that hitherto customary, to the process according to the invention no stage in the synthesis of the antibiotic side-chain any longer takes place in organic media, it is no longer necessary to carry out solvent recovery or disposal. The use of elevated pressure and elevated temperature increases the rate of the chlorination to such an extent that it takes place in a time comparable to that of the bromination.

It could not have been foreseen that it would be possible to carry out the process according to the invention with the specified advantages in such a straightforward manner.

The compounds of the general formula I are reacted, by the processes hitherto customary, with thiourea to give the corresponding thiazole ester, which is isolated as the solid and then subjected to alkaline hydrolysis to give the side-chain acid. The quality and purity of the resulting acid reach the standards customary in the current processes. The amides of this acid with 7-aminocephalosporanic acid or one of its derivatives represent the therapeutically very effective cephalosporin antibiotics.

The examples which follow serve to illustrate the invention further but without restricting it to them.

EXAMPLES

Example 1

Ethyl 4-bromo-3-oxo-2-syn-methoxyiminobutyrate 100 ml of technical ethyl 3-oxo-2-syn-methoxyiminobutyrate are introduced into a stirred vessel with internal thermometer. At room temperature, initially 2 ml of elemental bromine are added. The start of the reaction is evident from the decoloration and an increase in temperature of 6°–10° C. The mixture is not stirred during this induction period.

It is then cooled to 15° C., and 14–17 ml of bromine are metered in in such a way that the internal temperature does not exceed 20° C. The time required for this while cooling in water is about 30 minutes. The reaction is stopped when it is established in the HPLC that conversion of the organic component is complete. The hydrogen bromide which remains in solution is driven out with nitrogen for 30 minutes.

Example 2

Ethyl 4-chloro-3-oxo-2-syn-methoxyiminobutyrate 300 ml of technical ethyl 3-oxo-2-syn-methoxyiminobutyrate are introduced at 30° C. into a jacketed stirred vessel with internal thermometer. 160 g of chlorine are introduced in 7 hours under atmospheric pressure through an introduction tube with a sintered glass disk. The internal temperature is maintained at 32°–35° C. with a thermostat. The rate of introduction at the start of this reaction can be about 8–10 l/h, and still 1 l/h chlorine towards its end, without any considerable amounts of chlorine passing, with the escaping gaseous hydrogen chloride, into the absorber which is operated with sodium hydroxide solution.

The progress of the reaction can be followed by HPLC.

After all the chlorine has been introduced, nitrogen is introduced through the immersed tube for 15 minutes, and the dissolved gaseous hydrogen chloride is stripped off. There are obtained about 390 g of crude product which is stable on storage at room temperature and can be immediately processed further.

On purification, it distils over in a boiling range of 92°–96° C. under a pressure of 1 mbar. The distillate has the following $^1$H NMR spectrum (CDCl$_3$, 400 MHz): δ (ppm): 4.59 (s, CH$_2$Cl);

4.37 (q, 7.2 Hz, CH$_2$CH$_3$);

4.13 (s, OCH₃);
1.35 (t, 7.2 Hz, CH₂CH₃).

Example 3

Ethyl 4-chloro-3-oxo-2-syn-methoxyiminobutyrate 111 kg of technical ethyl 3-oxo-2-syn-methoxyiminobutyrate are introduced at 40° C. into a 250 l enamelled pressure vessel equipped as described. 42.8 kg of chlorine are introduced at a rate such that the internal temperature can be maintained at 50° C. by ice/salt cooling. The minimum time required is 1.5 hours. If the reaction has not yet started, which is evident from the evolution of heat, after introduction of 3.9 kg of chlorine, this must be stopped and restarted after addition of 0.1% sulfuric acid. If the reactor temperature falls below 40° C., due to excessive cooling, the introduction should not be continued until the contents of the vessel have been heated up.

The excess pressure in the vessel is maintained at 3 bar by an overflow valve. Gas flowing out is passed to a scrubber in which 120 l of 16% strength sodium hydroxide solution are circulated by pumping. There are obtained about 130 kg of crude product which can be reacted further without stripping or further purification.

We claim:

1. A process for the preparation of 4-halo-3-oxo-2-alkoxyiminobutyric esters by halogenation of 3-oxo-2-alkoxyiminobutyric esters, which comprises exposing the liquid substrate of a 3-oxo-2-alkoxyiminobutyric ester of the general formula I

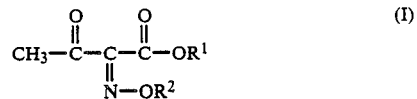

in which $R^1$ and $R^2$ represent $C_1$-$C_4$-alkyl, to the action of elemental halogen directly, without using a solvent, and thus obtaining a 4-halo-3-oxo-2-alkoxyiminobutyric ester of the general formula II

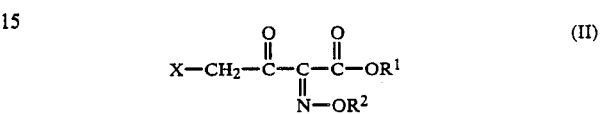

in which $R^1$ and $R^2$ have the previous meaning, and X represents halogen.

2. The process as claimed in claim 1, wherein the $R^2O$ group is in the syn position.

3. The process as claimed in claim 1, wherein $R^1$ represents ethyl and $R^2$ represents methyl.

4. The process as claimed in claim 1, wherein elemental chlorine or bromine is employed as halogen.

* * * * *